United States Patent [19]
Ellinwood, Jr.

[11] 4,003,379
[45] *Jan. 18, 1977

[54] APPARATUS AND METHOD FOR IMPLANTED SELF-POWERED MEDICATION DISPENSING

[76] Inventor: Everett H. Ellinwood, Jr., 3519 Tonbridge Way, Durham, N.C. 27707

[ * ] Notice: The portion of the term of this patent subsequent to Dec. 2, 1992, has been disclaimed.

[22] Filed: Sept. 24, 1975

[21] Appl. No.: 616,294

Related U.S. Application Data

[62] Division of Ser. No. 463,262, April 23, 1974, Pat. No. 3,923,060.

[52] U.S. Cl. .......................... 128/260; 128/DIG. 1; 128/2 R; 128/214 E; 128/218 A
[51] Int. Cl.² ..................... A61M 5/00; A61M 7/00
[58] Field of Search ........... 128/260, 218 A, 214 F, 128/DIG. 1, DIG. 13, 214 E, 213, 2 R

[56] References Cited
UNITED STATES PATENTS

| | | | |
|---|---|---|---|
| 2,690,178 | 9/1954 | Bickford | 128/213 |
| 3,651,806 | 3/1972 | Hirshberg | 128/214 E |
| 3,692,027 | 9/1972 | Ellinwood, Jr. | 128/260 |
| 3,701,345 | 10/1972 | Heilman et al. | 128/218 A |
| 3,731,681 | 5/1973 | Blackshear et al. | 128/214 F |
| 3,923,060 | 12/1975 | Ellinwood, Jr. | 128/260 |

Primary Examiner—Aldrich F. Medbery
Attorney, Agent, or Firm—B. B. Olive

[57] ABSTRACT

An apparatus for dispensing drugs and other medications within the body leaves the patient ambulatory and is adapted to be entirely implanted and to dispense such substances over a long period of time, e.g., one to several years, in accordance with the actual needs of the patient. A self-powered dispensing device stores a single or plural substances in powdered, liquid, or other dispensable form and utilizes a compressible container, i.e., a bellows, for withdrawing such substances from storage and dispensing to the body. The dispensing operation may be on a fixed schedule or may be controlled by monitoring single or plural sensors implanted in the body and evaluating the sensed data in order to control both the conditions under which and the kind of dispensing which takes place. Dual dispensers and dual medication may be employed.

22 Claims, 18 Drawing Figures

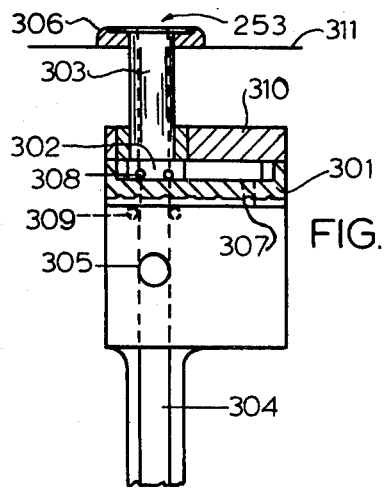
FIG. 14
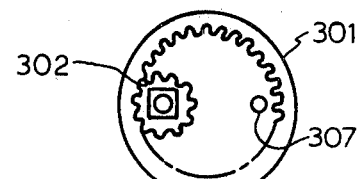
FIG. 14 A
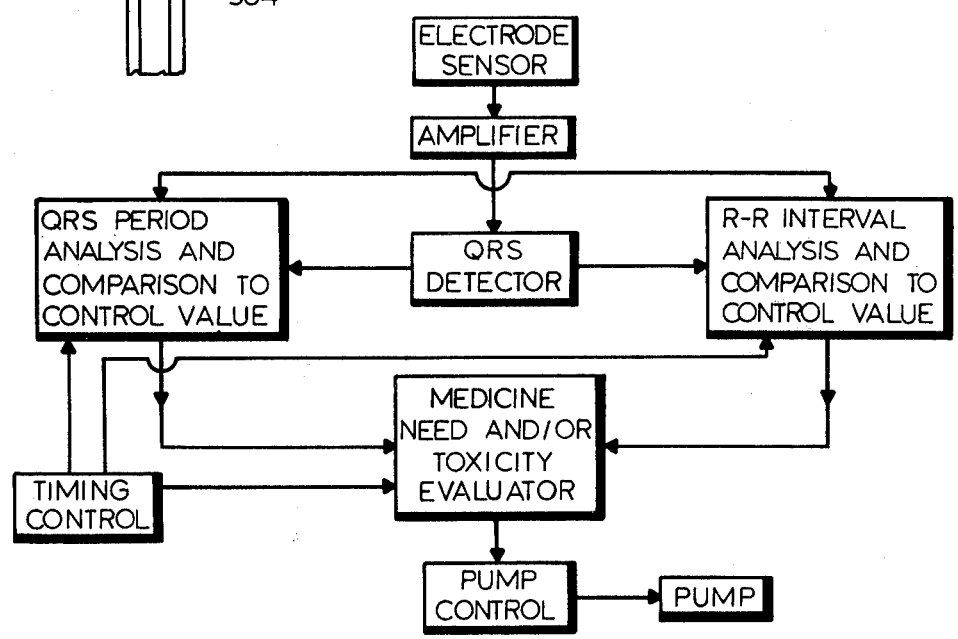
FIG. 15
FIG. 17
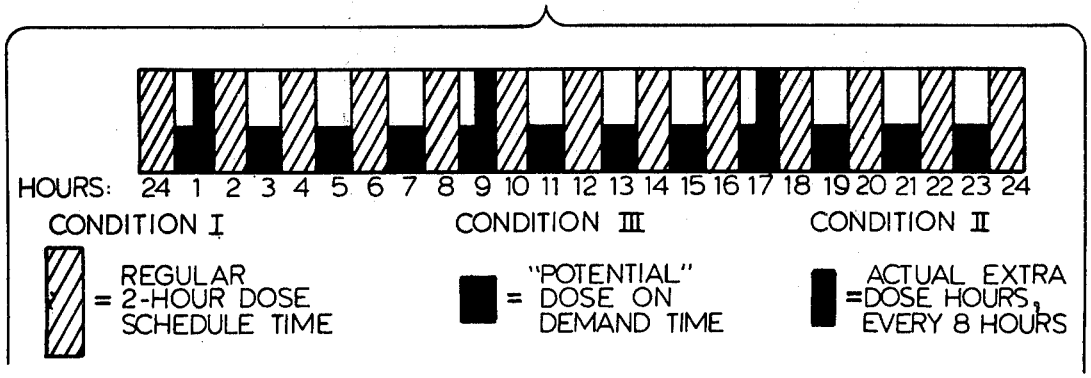

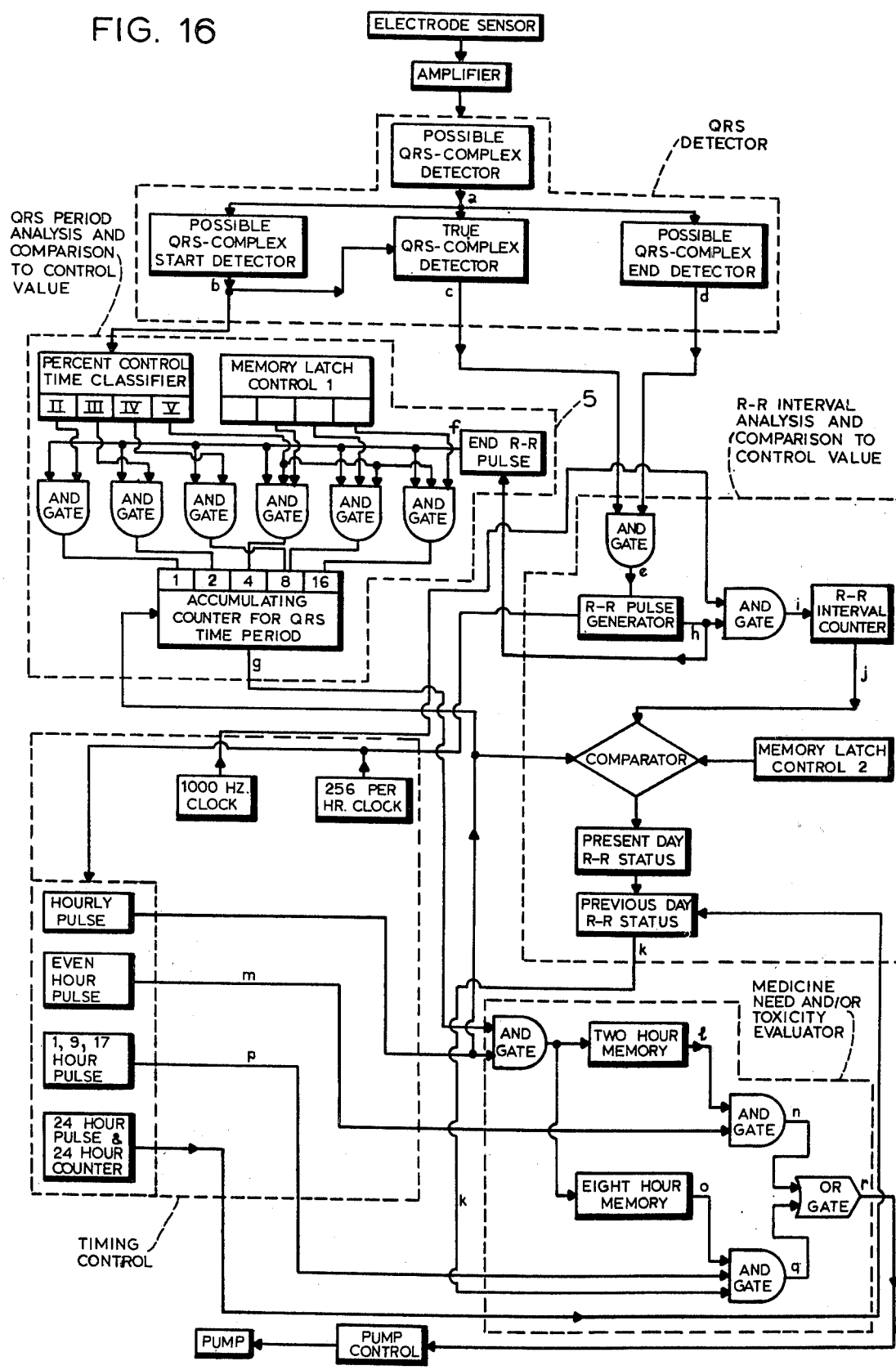

APPARATUS AND METHOD FOR IMPLANTED SELF-POWERED MEDICATION DISPENSING

CROSS-REFERENCE TO RELATED APPLICATION

This application is a voluntary divisional application of copending application, Ser. No. 473,262, entitled "Apparatus and Method for Implanted Self-Powered Medication Dispensing Having Timing and Evaluator Means", filed Apr. 23, 1974, now U.S. Pat. No. 3,923,060 dated Dec. 2, 1975.

BACKGROUND OF THE INVENTION

1. Field of the Invention

This invention pertains to dispensing medical or physiological substances or matter internally and more specifically to the mechanism used in implanted apparatus for dispensing these substances.

2. Description of the Prior Art

A review of prior art practices with regard to dispensing medical substances internally of the body is given in my prior U.S. Pat. No. 3,692,027 to which reference is made. So far as I am aware, my prior U.S. Pat. No. 3,692,027 provides the first teaching of a self-powered device which can be implanted and which is adapted to dispense medical substances in pre-measured doses at specific intervals over a long period of time. There has appeared in the June 1973 issue of Fortune magazine an article describing other continuous diffusion capsule types of dispensing devices. This article points out and emphasizes the tremendous need for long term medication dispensing devices which can provide for dispensing of medication at specific target organs or target sites. The prior art in the area of diffusion devices is also illustrated in Patent No. 3,379,996 by David Long and Moses Folkman for a polysiloxane carrier for controlled release of drugs and other agents. The device of this patent consists of a silicone rubber container with the drug being soluble and capable of diffusing through the silicone rubber to the outer surface of the container. A further development of this device was reported in the literature in the Annals of the New York Academy of Sciences, vol. 111, 1963-64 on pages 857-868 by Judah Folkman and David Long in which an electrical voltage is described as being applied to the container and to an outside electrode, in an attempt to increase the diffusion of materials through the fibrous scar tissue which is caused to be thrown up around the container by reason of its being implanted into the myocardium. The medication is described as being pulled through the myocardial fibrous scar tissue by means of iontophoresis. In these adaptations, the medication is in a continuous diffusion state and is not presented in discrete doses at timed intervals or according to the physiological needs.

Related to the present invention is the practice of implanting devices which sense heart conditions by means of the cardiac electrical activity and trigger electrical pulses to effect the heart rate according to the sensed data. These devices have generally been categorized a "pacemakers" and their use proves that the human body can accept implanted devices without endangering human life in the implantation procedure. They have also provided documentation for the applicability of feedback in the instance of the demand pacemaker version in which the output is controlled by the pacemaker logic which makes decisions on the basis of the electrical activity of the heart. The feasibility of the demand pacemaker for implantation is documented in the articles listed below.

1. Goetz, R. H.; Goldstein, J. V.; Frater, R. W. M., Berkovits, B. — *"Demand Pacemaking in Intermittant Heart-Block,"* Journal of the American Medical Association, Vol. 10, pp. 657–662, 1968.

2. Nathan, D. A.; Center, S.; Wu, C.; Keller, W.; "An *Implantable, Synchronous Pacemaker for the Long Term Correction of Complete Heart-Block.*" Circulation, Vol. XXVII, pp. 682-685, 1963.

3. Fischler, H.; Barr, I. M.; Auerback, Yerushalmi S.; Neufeld, H. N. — *"Atrial-Synchronized Demand Heart Pacing."* IEEE Transactions on Biomedical Engineering, Vol. BME-16, pp. 64–69.

A further area of the prior art related to the invention concerns the various types of sensors some of which are now commercially available and which can be used to accurately sense physiological and chemical body conditions. At present, the output of most of these devices that sense body changes are recorded and/or acted on by devices external to the body. For example, glucose detection, pH detection, ionic change detection, blood pressure or blood flow detection, electrical activity detection, respiratory detection, and gastrointestinal motility detection all constitute existing practical types of sensing apparatus.

It should also be recognized that the prior art has shown that an implanted device having a battery supply can be electrically recharged without having to remove the device. Also, my own U.S. Pat. No. 3,692,027 refers to means for recharging an implanted medication supply. Thus, both implanted battery and medication storage recharging are known.

From the foregoing, it can be seen that while the implanting technique has been perfected in many respects, and that while both the diffusion device which releases medication continuously and my own self-powered technique which provides a means for dispensing medical substances in pre-measured doses on a continuous basis or at predetermined regular intervals, no dispensing device or method has appeared in the prior art which allows medical substances to be dispensed by an implanted device and according to specific physical requirements of the patient that are determined by the device itself.

SUMMARY OF THE INVENTION

The apparatus and method of the invention is based on the apparatus being entirely implanted in the body and is primarily concerned with a bellows dispensing mechanism. The invention is explained with reference to a system having either one or a plurality of sensors adapted to sense body conditions and having a self-powered medication dispensing apparatus dependent on evaluation of changes in the sensed data and which can be directed to one or a plurality of medical substances in powdered, liquid, suspension, or other dispensable form. The invention is directed to single and plural bellows arrangements which act to withdraw and discharge the medications as part of the dispensing apparatus.

DESCRIPTION OF THE DRAWINGS

FIGS. 14 and 14A schematically illustrate a portal arrangement for replenishing medication to the system.

FIG. 15 is a block diagram of the decision making circuitry.

FIG. 16 is a more detailed circuit diagram corresponding to FIG. 15.

FIG. 17 is a representative timing diagram for dispensing plural doses of medication.

BACKGROUND FOR LATER DESCRIPTION OF THE PREFERRED EMBODIMENTS

Figure 1:
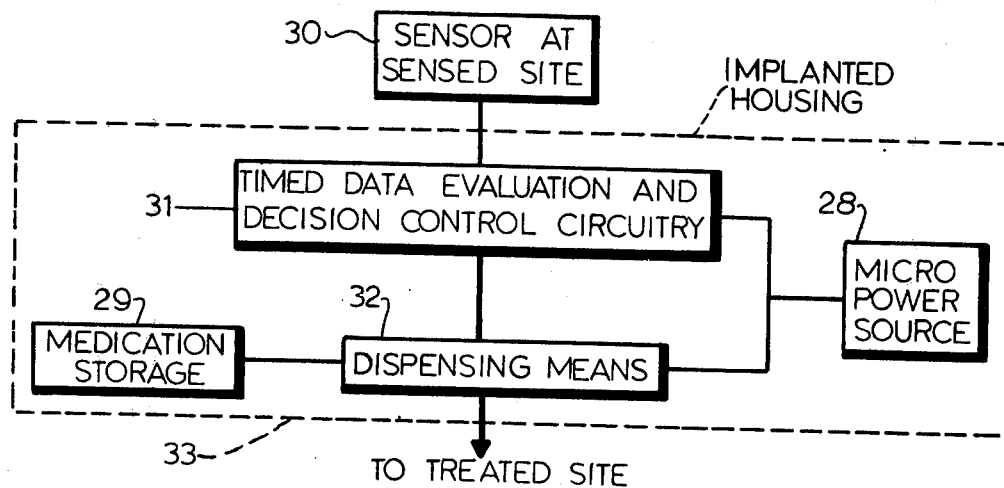
FIG. 1 is a block diagram illustrating the basic components of an apparatus according to the invention.

Prior to describing the apparatus and method which constitutes the invention, background information will be given concerning specific and recognized medical problems to which the invention method and apparatus may be applied. With this background, the mechanisms and methods later described will be better understood.

The general concepts behind the applications to be explained revolve around sensing and evaluation of biological signals that relate to abnormal processes or variations in normal processes in the body that may be used to evaluate the need for release of the given medication, hormone, or other type of chemical into the body or into specific organ or target sites. The dispensation of medication into specific organ sites, by the means of a small catheter, may of course allow for small quantities to be much more potent at the target site without systemic side effects developing. In addition, the concept of feedback evaluation controlling or altered release of medication will allow for an intermittent dispensing of the drug which might handle a problem at much lower doses than if medication is given over a sustained period without sensitive regard for therapeutic needs and the possible development of various toxic and tolerant effects. For example, an application that will be described later is that of transducing a pressure change in the blood vessels to provide information to the decision making capacity of logic and timing circuits in the device which activate a self-powered pump, to release a given quantity of a blood pressure reducing medication. The decision to dispense the medication is intended to operate only when the pressure rises above a certain level. This type of operation offers the opportunity to help overcome some of the undesirable effects from drugs such as adrenergic blocking agents, which when given chronically produce untoward side effects, including psychological depression and orthostatic hypotension. The same is true with a variety of other blood pressure reducing drugs. In other applications to be described later, physiological signals that predict the toxic effect of a given drug can be used by the device in evaluating the needed medication dispensation. Thus, the toxic effects can be counterpointed against the therapeutic need for medication by the logic system of the invention.

Involved in the biological sensing for blood pressure or other physiological changes that the device is evaluating, are possible training of physiological responses, effects or behavioral modification effects, by means of appropriate programming of such a device with small logic circuits. The type of signal detected and used for processing in the logic circuits may be either one signal or a combination of bio-signals, one or several being necessary for the triggering of the later described pump dispensing device. For example, by implanting an appropriate device in drug addicts one may monitor a variety of physiological changes produced by the injection of a narcotic; that is, respiratory depression measured by a micro strain gauge attached to the diaphram, a strain gauge attached to the stomach or in the upper duodenum to measure gastro-intestinal motility and the type of motility, and a pressure transducer to measure the increase in biliary duct pressure, and use the combination of these signals to detect the injection of a narcotic; the dispensing pump may then release a narcotic antagonist and/or, for behavioral training, may release a drug that would cause nausea and vomiting, thus providing for behavioral modification or avoidance conditioning.

The types of application used with evaluation of biological signals according to the invention include: 1) chemical transducers and feedback such as glucose detection, pH detection, ionic change detection; 2) temperature, pressure, or mechanical transduced changes; for example, blood pressure, blood flow gut motility; and 3) electrical activity as might be measured in the electrocardiogram or electroencephalogram. In the electroencephalogram and electrocardiogram, special logic circuits may be devised according to the invention on a miniature basis to provide for analysis of abnormal signals or rhythms and then the dispensation of a given amount of drug into the specific target organ. For example, with certain cardiac arythmias, the invention recognizes that it is possible to detect and evaluate these abnormalities with fairly simple logic circuits and then to dispense a drug into the pericardial sac in a similar manner that demand pacemakers now operate.

One of the disease types closely related to the invention is malignant hypertension. Malignant hypertension in the untreated state has a two-year mortality of 90% and a give-year mortality of almost 100%. Sympathectomy is capable of reducing the two-year mortality to 50% and the five year mortality to 80%. The newer anti-hypertension drugs have been more effective than this. What this invention provides is a method for treating malignant hypertension that is based on sensors inside the body and medication pumped to various effector sites. The sensors may include 1) blood pressure detecting devices in the neck and/or in the lower extremities; 2) electrical activity from the carotid sinus or aortic body; 3) possible electrical activity from the sympathetic outflow; and 4) the electrocardiogram. Blood measurements allow the mechanism of the invention to differentiate, for example, between the dystolic and systolic ratios. Combinations of information from the sensors may be programmed in micro-miniature logic circuits to provide a series of treatment decisions based on the individual characteristics of the patient.

On the effector side, the physician is given a wide choice with the present invention of attacking the problem of malignant hypertension in several sites: 1) the sympathetic outflow can be blocked with ganglionic blockers; 2) the adrenal outflow or releasing mechanisms can be blocked with ganglionic blockers; 3) appropriate drugs are available which can be dispensed systematically to block the adrenergic receptors throughout the body; and 4) another group of drugs known as the varatrum viride compounds are available and which may be dispensed according to the invention to inhibit the pressure centers in the brain itself. Taking only two of the mentioned examples, it is now possible to devise effector sites in 1) the sympathetic chain or outflow and 2) systemic sites via intraperitoneal dispensation. Using four sensors and two effector sites it is now possible to set up an array of contingencies, only some of which will be described. For example, if the dystolic blood pressure increased beyond a certain point, the systemic circulation, actually a site in the interperitoneal cavity, may receive a dose of beta adrenergic blocker antihypertensive medication; in addition, by means of carefully monitored release of drugs to the sympathetic outflow via a catheter, it is now possible to increase the effectiveness of the antihypertensive drugs by blocking this outflow. As discussed previously, this local application could help to prevent many of the serious side effects of systemic ganglionic blocking medication. Problems in hypotension may be monitored with neck blood pressure devices or with the electrical activity from the carotid sinus. Various features in the contingencies may be based on the normal exercise patterns of the individual, for example, in persons who have a heavy exercise load, the logic mechanism of the invention may be established to respond only after two or three or even 4 hours of increased dystolic pressure thus allowing for extending periods of exercise with slightly increased pressures. Combinations of the devices shown in the drawings may be used to supply drugs at the various effector sites.

In one specific adaptation a blood pressure sensor picks up both the systolic and dystolic blood pressure levels which are then amplified, or at least the analog signal is amplified, and presented to a detector and logic timer system using microminiature logic systems in which several decisions are made:

1. Is blood pressure above criteria level less than 30% of the heartbeats over a given period of time? If the answer to this is negative, then there is no release from the later described pump system. The reader should keep in mind that the pump system might operate 6 times a day, or alternately, it could operate twelve times a day, thus medication decisions could be made even 2 or 4 hours or even in fractions of hours.

2. Is the blood pressure above criteria level more than 30% of the time? If so, the medication is released into the systemic system.

3. Is the blood pressure above criteria more than 90% of the time? We would expect that the decision would be affirmative only in a rare number of occasions, but if the decision is affirmative then there is a release of another drug, a ganglionic blocking agent directly to the sympathetic outflow in the sacral region and the first five of the thoracic lumbar outflow.

The self-powered dispensing device of the invention allows for two major changes in the treatment of hypertension: 1) It allows for dispensing of the drug to a selective site inside the body, thus reducing many of the side effects of more potent and hypertensive drugs 2) It allows for a much more careful titration of the hypotensive effects of the drugs, thus cutting down on the number of unwarranted hypotensive episodes, especially those associated with postural hypotension. One means by which this may be accomplished is by selecting the drug used for its hypotensive effects for shorter duration of action, thus allowing for blood pressure feedback to regulate dosage.

One notable example of the foregoing is in the treatment of severe hypertension. Currently the drug most often used in the treatment of severe hypertension is guanethidine, which is a long-acting drug that tends to accumulate in tissues and is excreted slowly. Leaving off a dose of this medication would not have a major effect for several hours, thus the potent side effects could continue for a considerable period of time. Such drugs as bretylium, a short-acting hypertensive agent, have now been abandoned because of their potent side effects and poor absorption after oral administration. These effects may, however, be titrated in the self-powered dispensing device of the invention. In addition, other drugs similar to this compound, for example Bethanidine, (1-bensyl-2, 3-dimethylguanethidine) and other congeners may be used to a much better advantage by means of selective titration which lends itself to the apparatus and method of the invention.

The other groups of drugs that increase efficacy depend on the selective ability of the device of the invention to dispense medication in a particular site and which group includes the ganglionic blocking agents such as hexamethonium and related compounds. Blockade of the sympathetic ganglia has a marked interrupting effect on the adrenergic control of arteriols and results in vasodilation and improved peripheral blood flow of vascular beds and a fall in blood pressure. Part of the potency of these drugs is related to the low ratio of preganglionic axons to post-ganglionic axons. Thus, ganglionic block has a very potent effect. The major difficulty with the ganglionic blocking agents is a non-selective effect on both parasympathetic as well as sympathetic ganglions. Again, this group of drugs is poorly absorbed from the gastrointestinal tract, and there is a limited ability of these quaternary ammonium ions to penetrate cell membranes in general. By directing the outflow portal of a polyethylene catheter from the dispensing device of the invention to the sacral ganglion and to the first four ganglia of the thoracolumbar outflow the physician may selectively block blood vessels in large muscle of the extremities without major effects on the gastrointestinal tract, genitourinary system, or the heart and lungs.

Cancer is another problem that may be helped with the invention's method and mechanism. For example, there may be a need to dispense different types of drugs to different body sites depending on the site vulnerability. The bi- or tri-partite bellow bags, later described, may be used for this purpse. In other applications, the radio-activity of certain radio-active anticancer compounds may be monitored and the drug dispensed dependent on the radio-active concentrations in a given cancer site.

Another use may be in peptic ulcer or gastric ulcer. For example, the pH may be monitored in the stomach according to the invention and the antrium of the stomach may be bathed in an anti-cholinergic drug. Another use may be to bathe painful spinal dorsal nerves with medication in nerve injury triggered externally by the patient but with the availability still controlled by the invention's timing and logic circuits to prevent overdose. In this case, the patient's capacity to perceive pain would become the sensor. He would activate a reed switch to signal the device. With kidney stones, an outflow catheter may be placed into the kidney pelvis itself, monitored and used to change the pH of this area to dissolve the stones. Certain forms of epilepsy or perhaps several forms of mental illness may be more effectively treated with intraventricular medication or minute doses to a specific brain site. This medication in the case of epilepsy may be triggered by abnormal electrical activity. Other abnormal brain conditions may be treated by triggering off abnormal slow waves (in the awake state) or by programs to maintain certain forms of electrical activity such as alpha waves or certain sub-cortical rhythms. It, of course, should be understood that any of the central nervous system applications could only proceed after years of careful experimentation.

In the case of certain spastic vascular disease such as Berger's or Raynand's disease, it now appears feasible with the present invention to accomplish a periodic lumbar or cervical sympathetic block with medication applied to this area. Medication may be applied to the artery itself by implanting the outflow at the time of vascular surgery. Medication would be dispensed dependent on blood flow sensing.

Congestive cardiac failure may be detected with sensors that pick up venous pressure and cardiac electrical activity, and controlled with digoxin fed by catheter directly to the pericardial sac. In other conditions, depending on the results of extensive research, vasodilators may be dispensed to the pericardial sac by external patient control on the basis of angina or other perceived or sensed difficulties by the patient.

Finally, there are a variety of cardiac conditions, especially cardiac arthythmias, that may be treated by dispensing medication into or through the pericardial sac in response to abnormal electrical signals from the heart. For example, the device of the invention may dispense quinadine in the supraventricular tachycardia condition based on the electrophysiological activity of the heart. This example is later disclosed to demonstrate the present application of the concepts described above in a specific device whose operation can be fully documented.

In summary, many potential applications present themselves immediately and while many years of work will be required by many persons to fully develop the invention in all its ramifications, the basic concept is also immediately recognized as practical and useful. Those skilled in the art will recognize that the individual components required and the individual method steps required have been separately proven in other medical environments. It is the present invention, however, that combines such components and steps together to accomplish results and functions not heretofore achieved.

DESCRIPTION OF THE PREFERRED EMBODIMENTS

The invention wll first be explained in a broad context and in relation to certain applications following which reference will be made to construction details of specific components for practicing the invention, then finally one detailed application will be presented.

FIG. 1 illustrates in block and schematic diagram form the basic components of an implantable system according to the invention. In particular, there is provided a micro-power source 28, a medication storage 29, a sensor 30, a dispenser control 31, and a dispenser 32. All of the components except sensor 30 are contained in an appropriate housing 33 which is implanted in the body of the persons being treated. Power for the system is provided by a suitable micro-power source 28 such as described in U.S. Pat. 3,692,027. The purpose of the sensor 30 in each instance is to sense some type physiological, chemical, electrical, or other condition in the body at a particular site, and produce data which corresponds to the sensed condition at the sensed site. This data, according to the invention method, is then sampled and evaluated by an appropriate dispenser control 31, e.g., a logic circuit, and depending on whether the sensed data is or is not indicative of a need for medication, the dispenser control 31 will operate in a manner to cause the dispenser 32 to either remain off or to be operated to dispense some predetermined amount of medication from the storage 29 according to the patient's needs.

Figure 2:
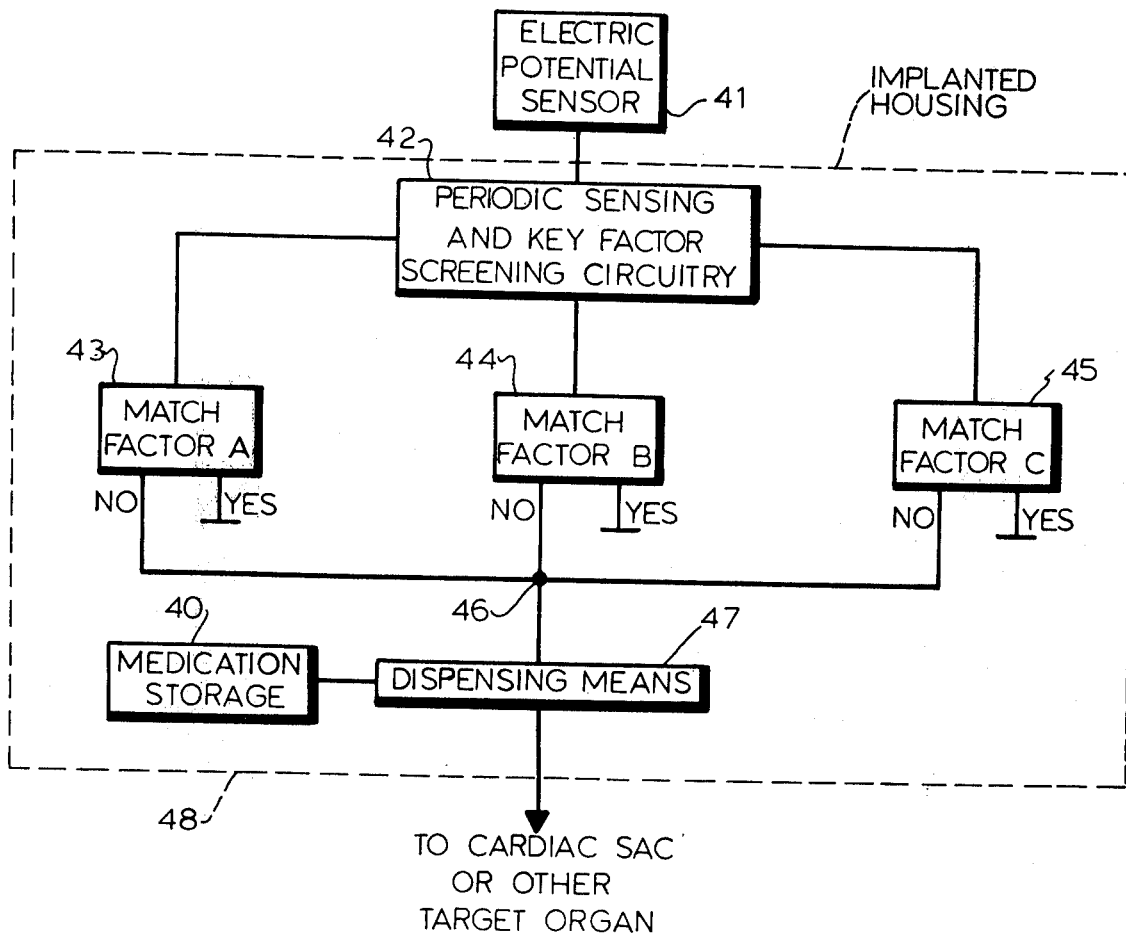
FIG. 2 is a block diagram illustrating the application of the invention to cardiac monitoring and medication.

Referring next to FIG. 2, there is schematically illustrated a more specific and somewhat more complex application of the invention to cardiac monitoring and medication. The micro-power source, while not shown for simplification, should be treated as part of the FIG. 2–6 systems. In the application of FIG. 2, there is provided medication storage 40 and an electric potential sensor 41, such as employed in electroencephalogram and electrocardiogram examinations. While indicated as a single sensor, sensor 41 could comprise plural, e.g., three or more, sensors. The sensed information is directed to an appropriate logic circuit 42 which is designed to screen the sensed data for key factors. Since logic circuits as such are known and within the skill of the art to design, the description in general will speak more to the medical aspects than to the precise details of the circuitry, although a more complete circuit disclosure will be provided in one example to be presented later.

With further reference to FIG. 2, it is known that sensed electric potential data such as obtained in electroencephalogram and electrocardiogram examinations will reveal a plurality of factors. The assumption of which FIG. 2 is based is that there are three factors A, B and C, which can be screened out and matched in appropriate subsidiary logic circuits 43, 44, 45 against normal limits. For example, subsidiary circuit 43 can match factor A as to whether it is or is not within normal limits (WNL) and produce a "no" or a "yes" output accordingly. Subsidiary circuits 44 and 45 can be designed for similar functions with respect to factors B and C such that if factors A, B and C are all outside normal limits an output is produced at junction 46 and which can be used to conrol the dispenser 47. Other combinations are possible. All of the components except the sensor shown in FIG. 2 should be noted as being enclosed in a suitable implantable housing 48.

Figure 3:
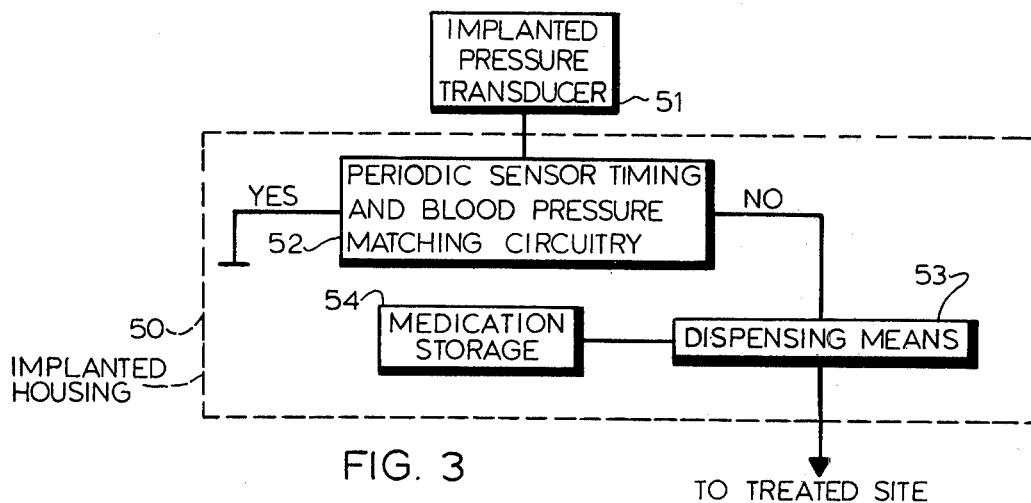
FIG. 3 is a block diagram illustrating the application of the invention to blood pressure monitoring and medication.

To illustrate a further application, reference is made to FIG. 3 which is directed to a blood pressure monitoring and medication system. In this application, there is provided a pressure transducer 51 which is connected to an appropriate logic circuit 52 contained in an implantable housing 50 and which is designed to make decisions on the basis of systolic and diastolic characteristics. If the blood pressure is not within the defined limits a no output is produced and which is used to operate a suitable dispenser 53 having medication selected from storage 54 to reduce the pressure.

Figure 4:
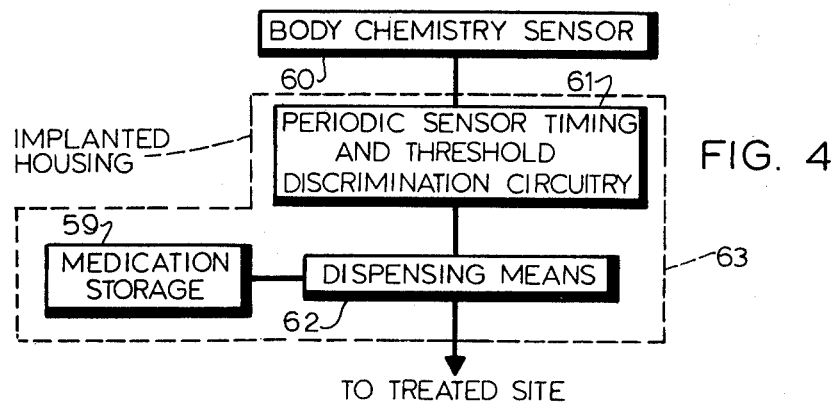
FIG. 4 is a block diagram illustrating application of the invention to body chemistry monitoring and medication.

In FIG. 4 a chemical monitoring system is illustrated. In this embodiment a suitable chemical level sensor 60 is employed and which, for example, may sense pH changes, ionic changes, glucose level or other body chemistry factors susceptible to sensing. The sensor 60 is connected to an appropriate threshold discriminator and logic circuit 61 which in turn is connected to a medication dispenser 62 and all of which components except the sensor are contained in a suitable implantable housing indicated by 63 which also houses the storage 59. In this application, the logic circuit 61 determines whether the sensed chemical factor is or is not within an acceptable threshold and, if not, operates the medication dispenser 62 to bring such factor within an acceptable threshold.

Figure 5:
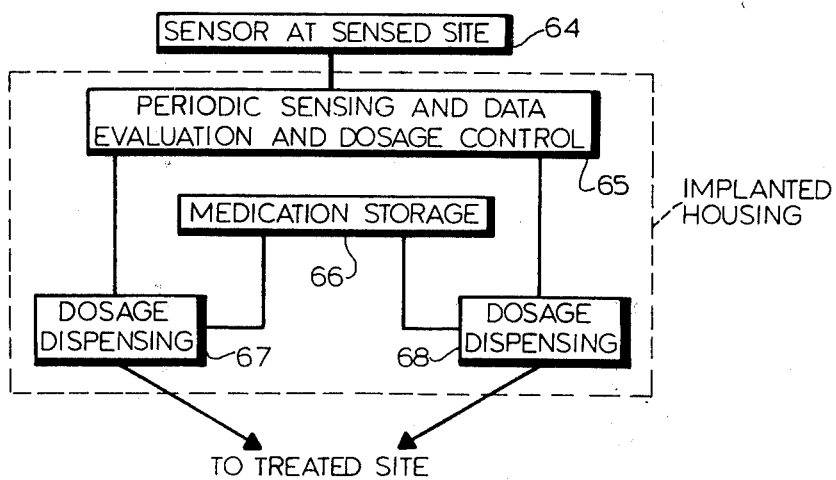
FIG. 5 is a block diagram illustrating application of the invention to dispensing medication to the same site from multiple sources.

Making reference next to FIG. 5, there is shown in block diagram form an application of the invention wherein dosages of the same medication may be dispensed from different sources. In this embodiment, the sensor 64 is connected to appropriate logic circuitry 65 which controls periodic sensing, evaluation of the sensed data and dispensing of medication from a common medication storage 66 through a dispensing means 67 or a separate dispensing means 68. For example, dispensing means 67 may constitute a low volume, regularly dispensed medication whereas dispensing means 68 may be used for supplementary medication at the same treated site.

Figure 6:
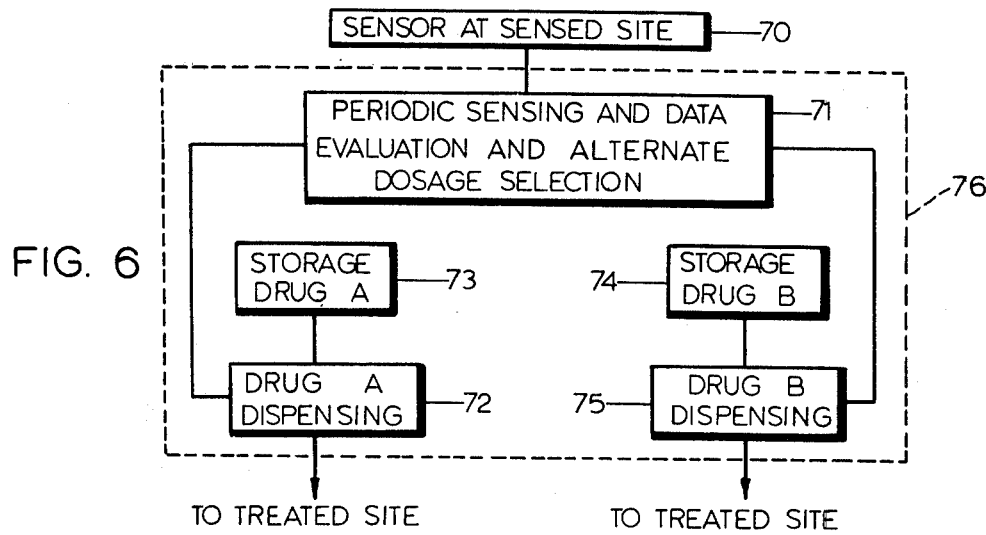
FIG. 6 is a block diagram illustrating application of the invention to dispensing different medications to different sites.

In FIG. 6, the sensor 70 is connected to the appropriate logic circuit which controls a dispensing mechanism 72 for dispensing from a drug storage 73 having, for example, drug A. Circuit 71 also controls the dispensing mechanism 75 for dispensing from an alternate drug source 74, for example, drug B. In this application it can be seen that different medications can be dispensed to the same or different treated sites with one medication being for one purpose and another medication being for another purpose. Housing 76 encloses the apparatus.

From the foregoing description, it can be seen that the various applications of the invention will each require appropriate timing and sensing devices, appropriate circuitry for evaluating and making decisions about the sensed data, and appropriate dispensing devices for dispensing medication subject to the evaluation of the sensed data. Implantable sensors for a great variety of purposes are well known and those skilled in the art will quickly appreciate their applicability to the broad concept embodied in the present invention. Those skilled in the art will also readily ascertain other types of implantable sensors which are suited and the required parameters for other types of sensors.

Considering next the type of logic circuitry required, given the concept of the invention, the design of such will be readily apparent to those skilled in the art. In general, the logic circuitry will be of a type in each application suited to receiving sensed data from a sensor, e.g., a transducer, in a form corresponding to the particular application, e.g., pressure data, chemical data, electrical data, et cetera, and producing an output depending on the data evaluation. In some instances, as previously noted in connection with FIG. 2 there may be a plurality of output data on a single output which can be screened by different subsidiary circuits for different data, e.g., factors A, B and C, as in FIG. 2. Miniature logic circuits of the kind required by the present invention may be found in both electronic design books as well as in medical literature, e.g., designs for demand pacemakers. Those skilled in the art will als readily appreciate the fact that the present invention is of such wide scope that the logic circuit designer is given a wide choice in the types of circuitry which may be used to perform the logic functions.

Another important consideration concerns the implantability of the sensor employed, the implantability of the housing which houses the medication storge and dispensing apparatus and the implantability of any catheter or other device employed to discharge the medication at the treated site. Since sensors, particularly electrical sensors, long term implanted diffusion devices, and the like, have all been used and the implanting problems are well known, the parameters required for implanting are considered known to those skilled in the art. Also, since pacemakers have been implanted, the general parameters for implanting a housing of the type required by the present invention is also well known. The long term discharge of medication internally through implanted catheters, and the like, fed by external sources of medication is also a current practice. Thus, tissue growth problems, tissue blockage problems, and the like, of the kind encountered in prior practices are contemplated by the present invention and the same technology previously developed will be useful in the present invention.

Each application of the invention requires means for storing a treating substance under pressure in powdered, liquid, or other dispensable form, means for pumping or otherwise removing predetermind portions from such storage and means for directing the measured dosage to the appropriate organ or site best suited to receiving the dosage. The amount of pressure may vary with the medication because of different viscosity, dose sizes, etc., and many arrangements known in the pumping art will suggest themselves. For example, the medication may be enclosed in an elastic sack by introducing an inert gas within the storage area to assert pressure.

The most immediately available device suited to the invention for storing and dispensing medication is illustrated in my prior U.S. Pat. No. 3,692,027. For example, such a device as shown in my prior patent may constitute the dispenser 32 illustrated in FIG. 1 and the dispenser control 31 in FIG. 1 may include a switch device connected so as to connect and disconnect the battery which is used to power the device of my prior patent. In this application, the sensor 30 of FIG. 1 senses the particular condition at timed intervals and the dispenser control 31 of FIG. 1 causes the dispenser mechanism, such as illustrated in my prior patent, to either operate or not operate according to the evaluation and decision based on the sensed data. Appropriate controls are preferably provided for in the circuit logic to prevent overdose if the sensed physiological change does not occur quickly enough in response to the medication dosage, e.g., appropriate timing delays or dose/time functions.

Figure 7:
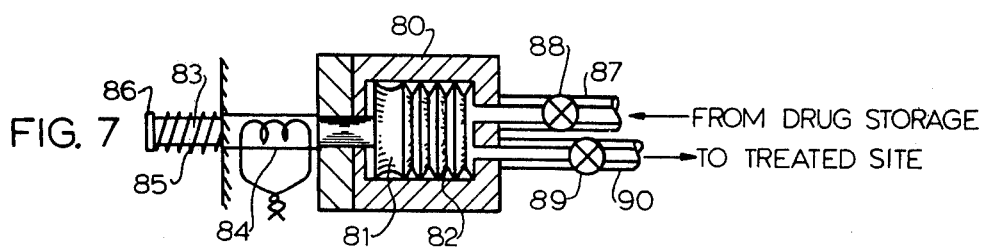
FIG. 7 is a somewhat schematic and enlarged diagram of a minature bellows pumping device useful in the invention.

The invention readily lends itself to a variety of dispensing mechanisms. Mention has already been made of the mechanism described in my prior U.S. Pat. No. 3,692,027. Another mechanism for pumping fluid medication is shown in FIG. 7. In FIG. 7 there is shown in a highly enlarged form a housing 80 mounting a piston 81 secured to a bellows container 82 made of polyvinyl or other suitable material. A rod 83 attaches to piston 81 and is caused to move inwardly by an appropriate solenoid 84 and to move outwardly by an appropriate spring 85 acting against a head portion 86 as schematically represented in FIG. 7. Solenoid 84 is, of course, controlled by an appropriate logic control as previously explained. The bellows 82 receives medication through an inlet tube 87 and a one-way valve 88 and discharges such medication through a one-way valve 89 and a discharge tube 90. It should, of course, be understood that the pump structure shown in FIG. 7 will in practice be contained in the implanted housing previously referred to and has the particular advantage of not requiring a high friction producing seal between piston 81 and housing 80 since all medication will be sealed and confined to the interior of bellows 82. Bellows pumps as such are known and proven.

Figure 8:
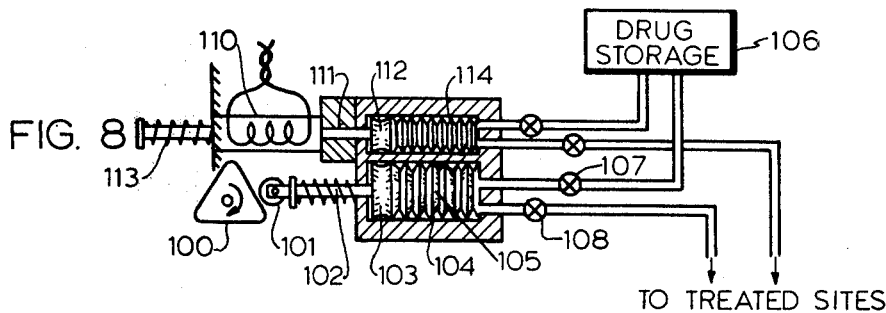
FIG. 8 is a somewhat schematic enlarged view of a multiple bellows type pump for dispensing the same medication to treated sites but in different quantities and under different conditions.

One problem common to many types of physical disabilities is the need to dispense a daily average dose, e.g., insulin, on a regular basis and to dispense intermittently dosages of short acting drugs, e.g., insulin, when need arises. FIG. 8 schematically represents a device suited to this requirement. In particular, cam 100 is driven by a suitable micro power motor such as shown in my prior U.S. Pat. No. 3,692,027 and which is arranged to be energized through an appropriate logic circuit, not shown. Rotation of cam 100 engages roller 101 and forces arm 102 to move piston 103 which causes the bellows 104 to discharge from the drug storage area 105 a predetermined dosage previously obtained from a drug storage 106. As cam 100 rotates and after discharge bellows 104 retracts and refills the chamber 105 at a suitable time the control for cam 100 causes it to stop. Appropriate one-way valves 107 and 108 control the intake and discharge. Such a cam driven arrangement may thus provide the required daily average dosages. For intermittent additional needs, a solenoid 110 is connected to the appropriate logic circuit, not shown, and when energized will move arm 111 and operate piston 112 to provide a lesser amount than is obtained by cam 100 so as to provide a smaller dosage. Solenoid 110 is de-energized at the end of the discharge stroke and spring 113 causes the storage area 114 to refill.

Figure 9:
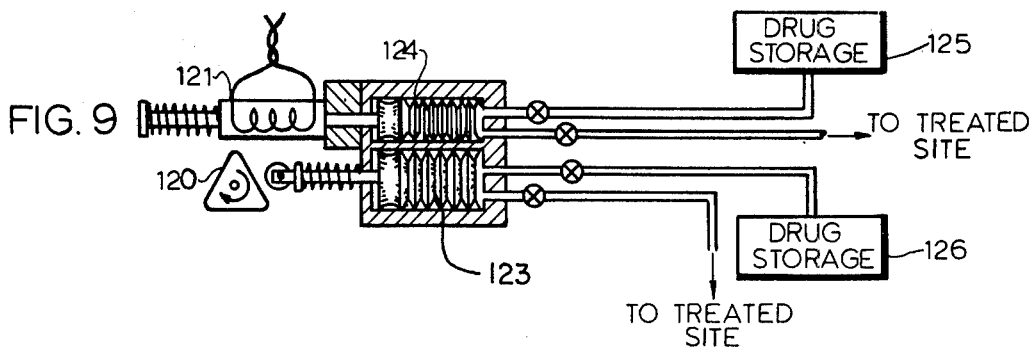
FIG. 9 is a somewhat schematic enlarged diagram of a multiple bellows type pump for dispensing separate kinds of medication to separate sites in different quantities and under separate controls.

In FIG. 9 there is indicated an arrangement for discharging two different types of medication. In FIG. 9, cam 120 and solenoid 121 should be considered similar in their operation to the cam and solenoid operations previously explained in connection with FIG. 8. In the FIG. 9 application, the cam 120 operates on the bellows 123 and solenoid 121 operates on the bellows 124. In the FIG. 9, as well as in the FIGS. 7 and 8 dispensing arrangements, power for the respective drive members, e.g., rod 83, cam 100, is provided by the previously mentioned micro-power source. One type of medication, e.g., a long acting drug, may be stored in one storage reservoir 125 and a separate medication, e.g., a short acting drug, may be stored in a separate storage reservoir 126. Thus, one drug source may be dispensed by use of solenoid 121 and another drug source may be dispensed by the use of cam 120. It will, of course, be understood that appropriate one-way valves and other features of known mechanical construction may be employed even though not shown or specifically explained.

Figure 10:
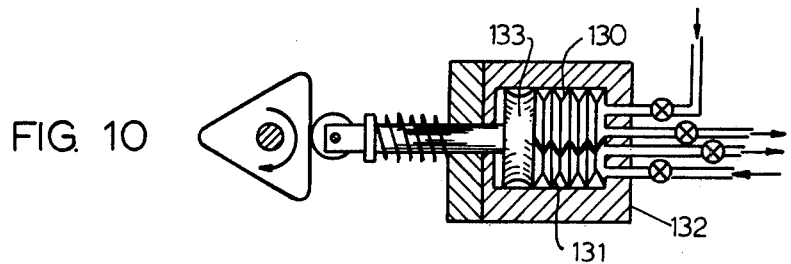
FIG. 10 is a somewhat schematic enlarged drawing of a bellows pump with multiple separated chambers for different chambers or sites having a common power source.

In FIG. 10 there is shown a reservoir arrangement comprising a bellows with two compartments 130, 131 housed in a common housing 132 and operated by a plunger piston 133. From the drawings, it can be seen that this arrangement, like that shown in FIG. 9, provides for dispensing two or more types of medication to two or more body sites. The FIG. 9 arrangement allows such medication to be dispensed to two sites at different pressures using two power sources whereas the FIG. 10 arrangement provides for the medication to be dispensed to two or more sites at unequal pressures using only one power source. In addition, the multiple chamber bellows of FIG. 10 provides for a two or more drug dispensing capability without the greatly increased friction of more cylinders and pistons. The bellows chamber in addition to its sealing functions allows for a variety of options at the time of implanting surgery simply by substituting various bellow configurations in the pump. This means that the surgical facility does not have to maintain many types of more expensive total pump configural changes. It is anticipated that a large variety of bellow shapes and sizes will be found useful and which can be substituted in the pump cylinder for a multitude of treatment purposes.

Figure 11:
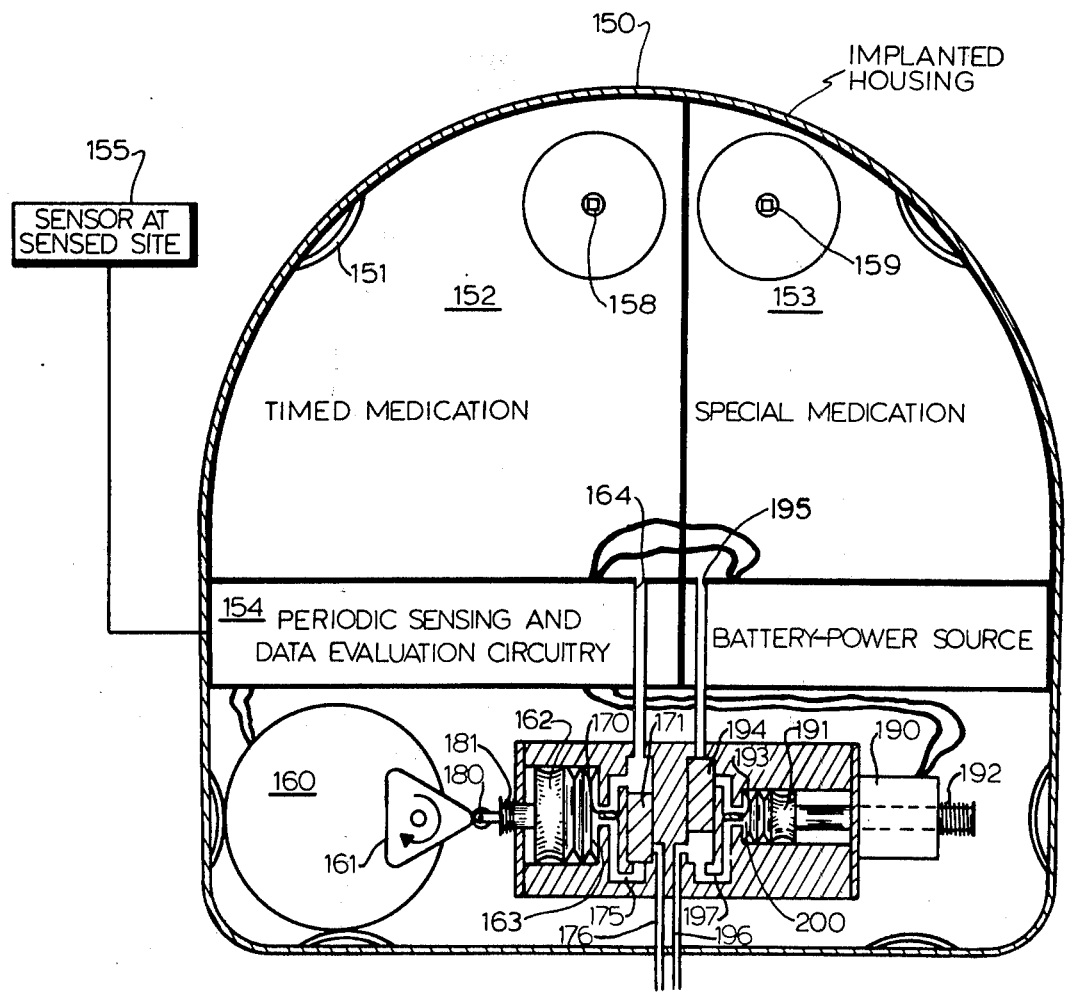
FIG. 11 is a somewhat schematic enlarged view of an implantable system according to the invention and adapted to dispense different medications from different sources under different controls.

In FIG. 11 there is schematically shown a system of a type which corresponds with the type of application diagram in FIG. 6. Here again it should be understood that the schematic diagram in FIG. 11 would, in practice, correspond to a device of substantially less physical size. In particular, there is represented in FIG. 11 a housing 150 having appropriate suture anchors 151. Within the housing 150 there is provided an appropriate compartment 152 for holding some predetermined amount of medication intended to be released over a long term for a chronic situation requiring regular dosages whose size can be predetermined and scheduled. The compartment 153 represents a storage area for special medication such as might be required by unusual and transient conditions in a specific patient. The previously mentioned evaluating and control circuitry is indicated as being confined in a separate compartment 154 and which is connected to an appropriate sensor 155 located within the body being treated but external of the housing 150. For the timed medication a micro-powered unit 160 of the type shown in my prior U.S. Pat. No. 3,692,027 is controlled by the circuitry in compartment 154 and when indicated by evaluation of information coming from sensor 155, unit 160 turns on and rotates the cam 161 thus driving the cam peaks against roller 180 attached to the shaft of piston 162 so as to discharge the medication confined in the storage area 152 through an appropriate discharge tube 164. During discharge the flap valve 170 closes as piston 162 moves to the right in FIG. 11 and a sliding cylindrical valve member 171 moves upwardly in FIG. 11 so as to allow communication between pipes 175 and 176. As cam 161 continues to turn roller 180 continues to ride on cam 161 by reason of spring 181. Flap 170 opens, sliding valve 171 moves down and a new charge is stored in the storage area 163. Portals 158, 159 provide for refilling.

When there is a demand for special medication as determined by sensor evaluation with the logic circuitry in compartment 154, slenoid 190 is energized which causes piston 191 to move to the left in FIG. 11 against the tension of spring 192. Flap valve 193 closes, sliding valve 194 rises as shown in FIG. 11 and pipes 196 and 197 are placed in communication to allow discharge through pipe 195. On the return stroke sliding valve 194 moves down, flap valve 193 opens and a fresh charge of the special medication is drawn into the storage area 200. Thus, by energizing and de-energizing the power unit 160 the treated body can be provided with the periodic timed medication and by energizing and de-energizing the solenoid 190, the treated body can be provided with the special medication.

There is next given a more detailed disclosure directed to a cardiac pump mechanism to dispense medication for prevention of recurrent tachycardias. As background, it should be noted that quinidine is given on a chronic basis for the prevention of recurrences of atrial fibrillation and flutter as well as supraventricular tachycardias not due to digitalis toxicity. Quinidine is also effectively used, as well as procainamide, in prevention of recurrences of ventricular tachycardia. Quinidine is also used to prevent recurrences of ventricular fibrillation except when ventricular fibrillation occurs during complete heart block in which case it is contraindicated. A discussion of treatment of cardiac arrythmias can be found in "Drugs Used in the Treatment of Cardiac Arrythmias" in Treatment of Heart Disease in the Adult, 2nd Edition, Rubin, T. L.; Gross, H.; Arbeit, S. R., Lea and Febriger, Philadelphia, pp. 297–324, 1972. One of the difficulties in using these drugs is that the therapeutic index, the ratio of therapeutic dose to toxic dose, is quite low. The pump feedback system of the invention is, however, adapted to carefully monitor the state of the heart and toxic manifestations of the drug and maintain the drug dosage at a level designed to minimize, if not eliminate, complications attributable to the medication. Thus, the device and method of the invention allows more general use of these medications in what are quite severe and life-threatening conditions of the heart. The invention is directed to what is needed, namely, a feedback evaluation system that will provide for the maximum needed therapeutic dose that can be maintained below the toxic manifestations of the drugs.

The described goals can be accomplished by monitoring the disease condition and regulating the medication to treat the condition according to the invention and yet steering clear of the toxic manifestations of the drug by monitoring and regulating the dose in relationship to these manifestations also. The disease entity to be treated as an example is the supraventricular tachycardias. The present example is directed to counter-pointing the heart rate against the toxic changes produced by quinidine, that is widening of the QRS Complex (a component of the electrocardiogram). The dose of quinidine can thus be monitored by use of the invention and reduced when there is prolongation of the QRS complex which occurs as the dose of quinidine begins to reach the threshold for toxic effects.

Figure 12:
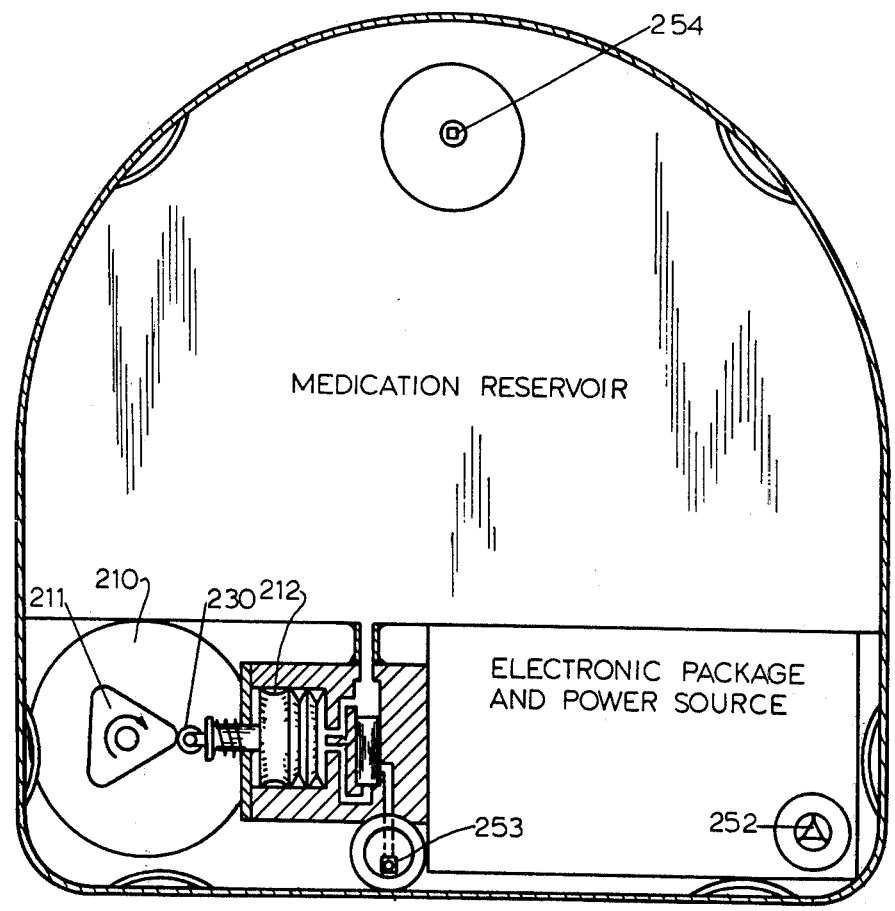
FIG. 12 is a schematic diagram of the apparatus of the invention as it might be used with superventricular tachycardias treated with quinidine.
Figure 13:
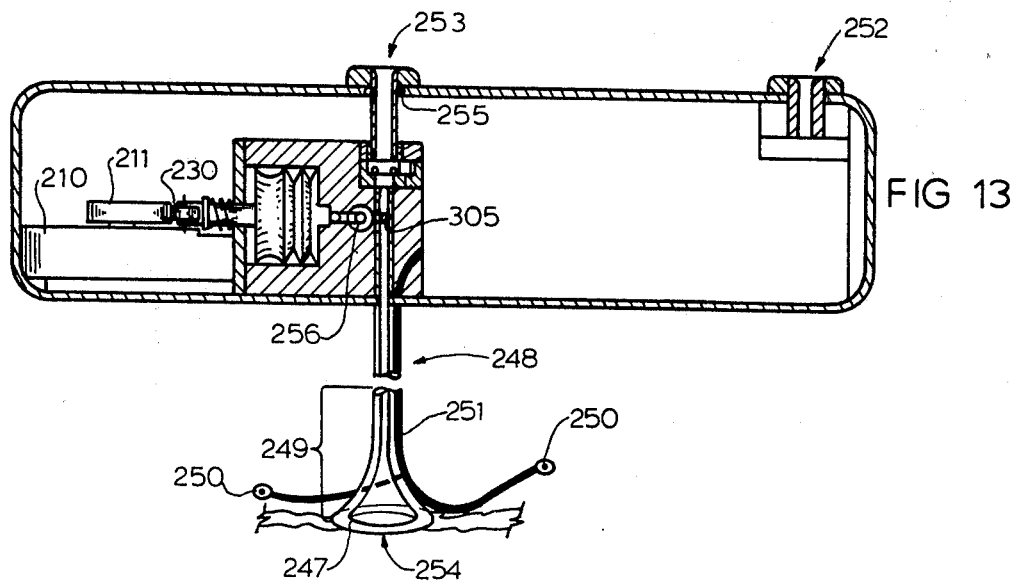
FIG. 13 is a schematic sectional view through the apparatus of FIG. 12.

FIGS. 12 and 13 demonstrate the basic construction and operation of the device to be used with supraventricular tachycardias treated with dispensed quinidine. The pump motor 210 is of the type shown in my U.S. Pat. 3,692,027 and is set to turn the equilateral cam 211, e.g., eight or more revolutions per day, thus providing a total of 24 potential cam pump activating contacts with the roller 230 which operates piston 212. Thus, the pump can potentially operate every hour of the day providing for 24 potential doses per day. Using this paradigm provides the following options, if one operates on a two-hour dispensing schedule, that is dispensing medication every two hours unless altered by decisions based on evaluation of the sensors (the twohour schedule is accomplished by turning off the pump motor 210 every other hour): 1. The mechanism would dispense very two hours as an average dose timing. 2. Depending on the feedback evaluation, it may suppress a dose of medication for 2 hours thus leaving a 4 hour interval between doses when this is indicated. 3. Extra doses can be dispensed on a 1 hour schedule if needed. In actual operation the movement of pump motor 210 will turn the cam 211 and dispense the first dose. Then the timing mechanism cuts off the mechanism for one hour unless conditions require that an extra dose of medication be provided and in this case the mechanism is designed to continue to operate for the next hour to provide an extra dose. Thus, under normal operating conditions, the mechanism will provide 12 daily doses every 2 hours. Should toxic conditions of quinidine manifest themselves, then the mechanism may be cut off for sufficient time to increase the interval between medications to 4 hours.

In actual practice with a supraventricular tachycardia, the electrodes 250 shown in FIG. 13 on the heart itself pick up electrical activity of the heart and conduct the heart signals to amplifiers in the electronic package by wires 251 embedded in the catheter 248. An electronic logic recognition program provides for identification of the QRS complex and another program subsequently quantifies the ORS period and R-R interval as described in relation to the chart shown in FIG. 17. Operationally, the cardiac frequency (R-R interval) is monitored and averaged for each hour over the 24 hour period and stored in a register. The lowest frequency average for an hour during the 24 hour period is compared with the lowest frequency hour from control periods as to whether this has increased by 10 to 20 percent over criteria control levels which criteria are set at time of implantation. Thus, if the frequency has increased by 20 percent, then the mechanism will provide three extra one hour doses every 8 hours for the next 24 hours. The decision-making control logic in the system provides for this operation. The contrasting concern, that of quinidine toxicity, is monitored by the QRS period. The QRS period is sampled and evaluated each hour and if it increases over criteria levels (% of control) or if premature ventricular contractions develop (indicated by very wide QRS complex over 150% of control) especially with the quinidine effect controlled, then the next dose period is suppressed by cutting off the power to the pump motor 210 and secondly stops the extra dose for that 8 hour period that is currently operational because of the criteria provided for in the first series of feedback options.

The chart depicted in FIG. 17 is explained as follows:

Condition I = Normal operation-pump operates every two hours on even hours.

Condition II = Cardiac frequency has increased by 10–20% which actually means the R-R interval has decreased by 10–20%. In practice, the hour with the lowest frequency for the previous 24 hour day is compared with the control value to make this decision. Then, if this 24 hour lowest hour frequency is 10–20% higher than control, the logic provides for three extra doses the next day given every 8 hours at 1, 9, and 17 hours.

Condition III = The sampled QRS period over the past hour is greater than criterion levels on the following basis; the QRS complex period is sorted on the basis of percent of control value and given a weight in the following schedule:

1. 110% or less than control value given weight of zero
2. 110-120% greater than control value given weight of one
3. 120-130% greater than control value given weight of two
4. 130-150% greater than control value given weight of eight
5. Greater than 150% of control value indicates ventricular premature contraction and is given a variable weight of 8 or 16. If over one hour, out of the 256 sampled QRS periods the weights add up to 256 or greater, then the pump is turned off for the next even hour operation and secondly stops the extra dose for that 8-hour period that might be currently operational because of criterion provided for in condition II. Thus, if the hour 4 dose was deleted, then the dose provided for at hour 9 would be deleted also.

Other aspects of FIGS. 12 and 13 that require explanation are the three input portals 252, 253, 254. Input portal 252 represents an eight position rotary switch and a needle contact. The rotary switch and needle contact operates by use of a solid core needle, not shown, with a round to triangular to round O.D. (outside diameter) tip section which is inserted into portal 252 which has a mating triangular hole as shown. Operation of the switch is accomplished by turning the needle through one to eight of the various positions. Contact to the switch function are through contacts on the three triangular surfaces of the needle approximated to the triangular hole contacts. The leads to the needle triangular surface are conducted down the long axis of the needle and are shielded by a suitable isoelectric material. Position No. 1 of the rotary switch provides for battery recharge through the needle contacts. Position No. 2 provides for monitoring the electrocardiogram from the implanted electrodes. Position No. 3 provides for stimulation through the cardiac electrodes if pacemaking functions are needed. Position No. 4 provides for contact with the logic system for calibration of the logic of the cardiac response parameters. Position No. 5 provides for monitoring the logic output and number of doses per day. Position No. 6 provides for cutting off of the entire system. Positions Nos. 7 and 8 are for future options.

Catheter access portal 253 is a bypass catheter inlet and provides the following functions: (1) It allows the physician to exert increased pressure if mechanical block occurs in the catheter. (2) It allows the physician to introduce a wire stylet if mechanical block occurs in the catheter. (3) It allows the physician to introduce additional drugs into the pericardial sac if needed. The catheter access portal operates in a manner best explained by reference to FIGS. 14 and 14A. A hollow bore needle, not show, with a round to square to round O.D. tip section is inserted through the patient's skin with the aid of protuberance 306 and thence into the square hole 303. The square needle segment engages the sides of the square hole 303. Rotating the needle about its long axis rotates pinion 302, which is meshed with and rotates partial ring gear 301. When partial ring gear 301 has rotated to its counterclockwise limit portal 307 is in line with the I.D. (inside diameter) of the needle allowing access to the catheter 304, and the pump output port 305. O-rings 308 and 309 seal the port in both open and closed configuration. Pinion 302 is held in position by top plate 310. In FIG. 14, the external casing of the device is represented by line 311.

For purposes of replenishing medication, the input portal 254 is employed. Since the introduction of pressurized replenishing medication has been previously discussed in my U.S. Pat. No. 3,692,027 and a suitable portal structure described, no further detailed description of this operation or of the refill portal is deemed necessary.

FIG. 13 shows in further detail the bypass system with the details of the attachment of the catheter system to the pericardial sac. O-rings 255 beneath the entry portal are provided for sealing purposes. A one-way valve 256 in the catheter leading to the pump provides for block of any increased pressure in the bypass system into the pump mechanism. The catheter system is sewn into the pericardial lining with a ring 247 embedded in the catheter 248 having both a uniform catheter section and an appended expanded catheter section in the form of a trumpet 249. The expanded catheter diameter provides for increased surface area and reduces any blockage due to the fibrosis around the exit portal to the catheter. Also shown adjacent catheter 248 are leads 251 leading from the pair of sensing electrodes 250 to the amplifier and logic system. These are actually embedded in the catheter and provide additional support for the catheter. The electrodes 250 and attached wires are embedded in a polyvinyl shield after their exit from the catheter.

A block diagram describing the general operation and decision making involved in control of the cardiac medication pump is illustrated in FIG. 15. The depicted "electrode sensor" and "amplifier" are intended to represent standard devices such as are used in present cardiac pacemaker circuits. The remaining portion of the block diagram of FIG. 15 is the "brain" of the system and provides control to the "pump" based on the presence of conditions I, II or III, as previously described. The type and nature of components required for the FIG. 15 circuit are generally known and have been elsewhere indicated. Therefore, since FIG. 16 represents a more detailed description of FIG. 15, it is believed those skilled in the art will readily understand the circuitry and operation depicted in FIG. 15 after reading the description to follow.

The description now turns to a description of FIG. 16 which constitutes a logic flow chart suited to the application related to FIGS. 12-15 and 17. Since the components in FIG. 16 are identified are are known to those skilled in the art and their relation in the circuit is shown, the description will next concern itself primarily with the operation of the circuitry of FIG. 16. The "Possible QRS-Complex Detector" with output at (a) detects the beginning and end of all "possible" QRS-complexes. The start of a possible QRS complex is detected by the Possible QRS-Complex Start Detector with output at (b) and the end of a possible QRS-complex is detected by the Possible QRS-Complex End Detector with output at (d). The decision of whether the possible QRS-complex that is detected is a "true" QRS-complex is made by the "True QRS-Complex Detector" with output at (c). The outputs at (c) and (d) are then combined through an And Gate with output at (e). This output (e) represents the end of a true QRS-complex.

The QRS-complex is analyzed in two different ways: (1) Measurement of the time period of the QRS-complex; and (2) Measurement of the time period between two consecutive QRS-complex, i.e., R—R interval.

The measurement of the time period of the QRS-complex is accomplished through the "Per Cent Control-Time Classifier." The signal at (b) is the signal to reset and then start this classifier which classifies the time period of a QRS-complex into one of five time intervals: (I) 110 or less of control time, (II) 110 to 120% of control time, (III) 120 to 130% of control time, (IV) 130 to 150% of control time, or (V) 150% or greater of control time. The control time is the time period of a normal QRS-complex for the given patient. The signal at (f) occurs at the end of a true QRS-complex once every 256 times an hour. The pulse at (f) is the signal to add to the "Accumulating Counter For QRS Time Period." Depending on the percent of control time classification of the QRS-complex, this counter is incremented by 0, 1, 2, 4, 8, or 16 counts. Each classification adds a set number to the counter. Classification (V) has the additional option of having its count value changed to 4, 8, or 16 through "Memory Latch Control 1". This memory latch control can be set through the previously mentioned externally accessible rotary switch 252, not shown in FIG. 16 but shown in FIGS. 12 and 13. If the count on the "Accumulating Counter for QRS Time Period" exceeds 256 in an hour then the output at (g) is a logic "1" otherwise (g) is a logic "0".

The measurement of the R-R interval is accomplished by the "R-R Pulse Generator" which selects two consecutive true QRScomplexes once every 256 times an hour and outputs a logic 1 pulse at h equal in length to the time period between the end pulses of these consecutive true end pulses. This pulse at (h) is then gated through an And Gate with a 1000 Hz. clock and the resulting pulses at (i) represent the number of 1000 Hz. pulses occuring during a R-R interval once every 256 times an hour. These pulses at (i) are accumulated by the "R—R Interval Counter" with output at (j). At the end of each hour the contents of the "R—R" Interval Counter is compared with the R—R Control Value . This control value represents the number of 1000 Hz. pulses that occur during a time period that is 20% less than a normal R—R interval for a given patient (i.e., a time period corresponding to a R—R frequency 20% faster than normal.) This control value is set through the previously mentioned externally accessible rotary switch 252 into "Memory Latch Control 2." If the hourly count is greater than the control value then the "present Day R-R Status" (which is normally a logic 1) is set to a logic 0. Once set to logic 0, it remains at logic 0 for the remaining portion of the present day. At the end of the 24th hour this value is stored in the "previous Day R-R Status" for use in making the present day's pump decisions at the beginning of hours 1, 9, and 17. This output at (k) is a logic 0 if any hourly R-R interval count for the previous 24-hour day was greater than the "R-R Control Value" for a given patient (i.e., if the average R—R frequency during any hour of the 24 hour day was slower than the 20% greater than normal control value).

The two outputs at (g) and (k) control the pump operation. Normal operation causes the pump to dispense at all even hours (Condition I in the FIG. 17 Chart). Increase in frequency for the lowest "hour frequency" for the 24 hour period of the previous day (indicating need for more medication), a logic 1 at (k), provides for the pump to dispense additional doses at hours 1, 9, and 17 (Condition II in the FIG. 17 chart). These two operations occur in the following manner: If either the output at (n) or (q) is a logic 1 then the input to the "Pump Control" is a logic 1 at (r). A logic 1 pulse at (r) is the signal to turn on the pump. This signal at (r) is a logic 1 at even hours (output (m) ), normally, and at hours 1, 9, and 17 (output (p) ) under Condition II of the FIG. 17 Chart unless these conditions are altered by one of the following restraints: If the output at (g) is a logic 1 for any hour then the output of the "Two Hour Memory" at (1) is set to a logic 0 for the next 2 hours (normally this output at (1) is a logic 1). This signal (1) is gated with the even hour pulse at (m) through an And Gate with output at (n). If the output at (g) is a logic 1 for any hour then the output of the "8 Hour Memory" at (o) is set to a logic 0 for 8 hours. (Normally this output at (o) is a logic 1.) This output at (o) is gated with the logic 1 pulse at hours 1, 9, and 17 at (p) and the pulse at (k) through an And Gate with output at (q).

With the foregoing in mind, it should be noted that the power unit 210 of FIGS. 12–13 and which is associated with the FIGS. 15–16 circuitry, is appropriately geared to operate on a fifty minute hour in contrast to the 60 minute hour for the logic circuit. This allows ten minutes between the end of the power unit hour and the end of the logic system hour which allows for any margin of timing error in the power unit movement due to increased work load.

In summary, there has been described an implantable system and method specifically useful for treating the human and animal body in a unique way. The "power source" may take many forms. It may be in the micropower form referred to in my prior U.S. Pat. No. 3,692,027 or in other equivalent miniaturized forms providing a long life, i.e., measured at least in terms of days and preferably years, source of electrical energy, for energizing the system electronics and for providing power for the drive member used to actuate the dispensing mechanism. The apparatus lends itself to a wide variety of applications and the medication may include pharmacologically active drugs needed, body constituents, energy compounds, radioactive materials, and the like.

It should also be noted that the term "body" and "animal body" as used in the claims are intended to include animal, human and other living bodies. Further, the term body is intended to encompass any environmental body, whether living or otherwise adapted to receiving a self, micro powered and timed device for incremental dispensing of substances into such body.

What is claimed is:

1. A self-contained and powered implant apparatus adapted to be totally received within a selected animal body, including human, for periodically dispensing selected medication therein while leaving the body ambulatory at all times, comprising:
   a. a unitary housing adapted to be completely implanted and secured within and to the body at a selected site and having therein various compartments enclosed by said housing and adapted for mounting a medication storage member, a micro size power source, miniaturized electro-mechanical driving and dispensing means adapted to being powered by such source for dispensing medication from such storage member and electrical means for connecting the driving means to the source so as to operate the dispensing means on a schedule according to the needs of said body for medication;
   b. a storage member mounted within the implanted housing for storing selected medication to be dispensed in selected quantities;
   c. a micro size power source mounted within the implanted housing and secured proximate said storage member and having a useful working life in terms of at least several days;
   d. miniaturized electro-mechanical driving means mounted within the implanted housing selectively connected to and powered by said source;
   e. miniaturized dispensing means mounted within the implanted housing and having a retractable flexible walled container means with an inlet connected to receive medication from said storage member and connected for being powered by said driving means and when so powered and when expanded, receiving from said storage member through said inlet and into said container means successive measured quantities of selected said medication and having an outlet means for enabling discharge of such medication from said container means through the wall of the implanted housing and into said body during compression of said container means; and
   f. electrical means mounted within the implanted housing for providing an electrical connection between said power source and said driving means for driving, energizing and actuating said dispensing means including said container means on a controlled schedule in coordination with the medical needs of the body.

2. An apparatus as claimed in claim 1 including one-way valve means associated with each respective said inlet and outlet and operable in coordination with operation of said container means.

3. An apparatus as claimed in claim 1 wherein said container means comprises a single bellows type container means.

4. An apparatus as claimed in claim 1 including externally available portal means in said housing adapted for replenishing medication in said storage member.

5. An apparatus as claimed in claim 1 wherein said container means outlet includes a discharge port and externally accessible portal means enabling the entry of a suitable tool to clean said discharge port.

6. An apparatus as claimed in claim 1 including externally available portal means in said housing adapted for replenishing medication in said storage member wherein said container means outlet includes a discharge port and externally accessible portal means enabling the entry of a suitable tool to clean said discharge port.

7. An apparatus as claimed in claim 1 wherein said container means comprises a dual bellows type container means with a common said driving means and with each member of the dual container means having a respective said inlet and outlet.

8. An apparatus as claimed in claim 4 wherein the members of the dual container means are sized for different size dosages.

9. An apparatus as claimed in claim 4 including one-way valve means associated with each respective said inlet and outlet and operable in coordination with operation of said container means.

10. An apparatus as claimed in claim 1 wherein said driving means comprise dual driving means and said container means comprise dual container means each having an associated said driving means and with each container means having a separate said inlet connection to said storage member and a separate said outlet connection through the wall of said implanted housing and said electrical means includes means for connecting each respective driving means to said power source on a schedule according to the medical needs of said body.

11. An apparatus as claimed in claim 10 wherein said respective container means are sized to measure different size dosages of said medication.

12. An apparatus as claimed in claim 10 including one-way valve means associated with each respective said inlet and outlet and operable in coordination with operation of said container means.

13. An apparatus as in claim 10 wherein one of said driving means is adapted for relatively fast actuation of its respective associated container means to effect relatively quick dispensing of a dosage and the other of said driving means is adapted for relatively slow actuation of its respective said container means to effect relatively slow dispensing of a dosage.

14. An apparatus as claimed in claim 13 wherein said relatively fast actuated driving means is of a solenoid type and said relatively slow actuated means is of a revolving cam type.

15. An apparatus as claimed in claim 1 wherein said storage member includes two compartments each with a storage of medication, said container means and driving means comprise dual container means with respective said inlets and outlets and with each container means having an associated driving means and said electrical means including means for connecting each respective driving means to said power source such that each medication in each compartment can be dispensed through its own respective container means and on its own schedule coordinated with the medical needs of said body.

16. An apparatus as in claim 15 wherein said respective container means are sized to measure different size dosages of the respective said medications.

17. An apparatus as in claim 15 wherein one of said driving means is adapted for relatively fast actuation of its respective associated container means to effect relatively quick dispensing of a dosage and the other of said driving means is adapted for relatively slow actuation of its respective said container means to effect relatively slow dispensing of a dosage.

18. An apparatus as claimed in claim 17 wherein said relatively fast actuated driving means is of a solenoid type and said relatively slow actuated means is of a revolving cam type.

19. An apparatus as claimed in claim 15 including one-way valve means associated with each respective said inlet and outlet and operable in coordination with operation of said container means.

20. The method of utilizing the apparatus of claim 1 of periodically dispensing medication in said body according to its needs while leaving the body ambulatory at all times, comprising the steps:
 a. implanting the housing of said apparatus in the body at a selected site and with a store of selected medication; and
 b. allowing said medication to be dispensed through said container means in successive measured dosages drawn into and discharged therefrom to a selected site within the body on a schedule controlled by said electrical means and over a long period of time.

21. The apparatus of claim 1 wherein said dispensing means is adapted for receiving interchangeable said container means enabling said measured quantities to be varied according to medication needs.

22. An apparatus adapted to be totally received within a selected animal body, including human, for periodically dispensing selected medication therein while leaving the body ambulatory at all times, comprising:
 a. a storage member mounted within implanted housing means for storing selected medication to be dispensed in selected quantities;
 b. a micro size power source mounted within implanted housing means and having a useful working life in terms of at least several days;
 c. miniaturized electro-mechanical driving means mounted within implanted housing means and selectively connected to and powered by said source;
 d. miniaturized dispensing means mounted within implanted housing means and having expandable - contractible flexible walled container means with an inlet connected to receive medication from said storage member and connected for being powered by said driving means for contraction and expansion operations and when expanding to receive from said storage member through said inlet and into said container means successive measured quantities of selected medication and having an outlet means for enabling discharge of such medication from said container means into said body during contracting of said container means; and
 e. electrical means mounted within implanted housing means for providing an electrical connection between said power source and said driving means for driving, energizing and actuating said dispensing means including said container means on a controlled schedule in coordination with the medical needs of the body.

\* \* \* \* \*

UNITED STATES PATENT OFFICE
CERTIFICATE OF CORRECTION

Patent No. 4,003,379     Dated Jan. 18, 1977

Inventor(s) Everett H. Ellinwood, Jr.

It is certified that error appears in the above-identified patent and that said Letters Patent are hereby corrected as shown below:

Col. 1, line 7, "473,262" should be --463,262--.

Col. 1, line 61, "a" should be --as--.

Col. 3, line 14, "minature" should be --miniature--.

Col. 5, line 2, "give-year" should be --five-year--.

Col. 5, line 57, "or" should be --to--.

Col. 6, line 8, "even" should be --every--.

Col. 8, line 18, "wll" should be --will--.

Col. 9, line 1, "of" should be --on--.

Col. 9, line 23, the quotation marks were omitted around the word "no".

Col. 13, line 15, "slenoid" should be --solenoid--.

Col. 14, line 47, "ORS" should be --QRS--.

Col. 15, line 31, "one" should be --the--.

Col. 16, line 67, second appearance of "are" should be --and--.

Col. 22, line 8, "and" should be deleted.

Signed and Sealed this

Twenty-sixth Day of April 1977

[SEAL]

Attest:

RUTH C. MASON
Attesting Officer

C. MARSHALL DANN
Commissioner of Patents and Trademarks